United States Patent [19]

Hannah et al.

[11] 4,292,270

[45] Sep. 29, 1981

[54] METHOD AND APPARATUS FOR MAKING COUDE CATHETERS

[75] Inventors: Richard E. Hannah, Spring Grove; Steffen Lyons, Grayslake, both of Ill.

[73] Assignee: Baxter Travenol Laboratories, Inc., Deerfield, Ill.

[21] Appl. No.: 51,331

[22] Filed: Jun. 22, 1979

[51] Int. Cl.³ .............................................. B29C 1/04
[52] U.S. Cl. ................................... 264/320; 264/296
[58] Field of Search ....................... 264/296, 320, 322

[56] References Cited

U.S. PATENT DOCUMENTS

| | | | |
|---|---|---|---|
| 2,532,844 | 12/1950 | Hulbert, Sr. et al. | 18/19 |
| 2,725,597 | 12/1955 | Douglass | 18/19 |
| 2,876,496 | 3/1959 | Murphy, Jr. | 18/56 |
| 2,972,781 | 2/1961 | Levy | 18/56 |
| 3,093,526 | 6/1963 | Price et al. | 156/85 |
| 3,149,186 | 9/1964 | Coanda | 264/320 X |
| 3,288,901 | 11/1966 | Clark | 264/267 |
| 3,300,559 | 1/1967 | Bachr | 264/323 |
| 3,509,252 | 4/1970 | Klimaszewski | 264/296 |
| 3,843,300 | 10/1974 | McFarlane | 264/322 X |
| 4,085,185 | 4/1978 | Adair | 264/320 X |

FOREIGN PATENT DOCUMENTS 752221  7/1956  United Kingdom .

*Primary Examiner*—Thomas P. Pavelko
*Attorney, Agent, or Firm*—Paul C. Flattery; John A. Caruso; Garrettson Ellis

[57] ABSTRACT

A method of making a elbowed end (coude) catheter which comprises: inserting an end of a flexible, thermoplastic tube into the bore of a closed-end, hollow, tubular die which defines the desired curve of the elbowed end catheter. The tubular die is heated to a temperature above the plastic melt temperature of the thermoplastic tube, while advancing the tube into the die, to cause at least about 0.5 cm. of the tube end to collapse into a generally solid, curved mass. The die and tube contained therein are then cooled to a temperature below the plastic melt temperature, and the tube is withdrawn having a closed, formed coude tip.

15 Claims, 3 Drawing Figures

FIG. 1
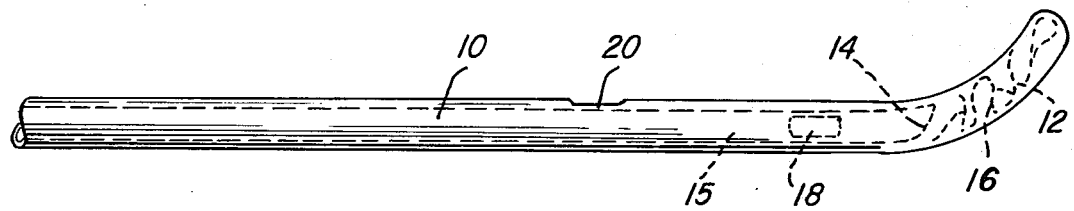
FIG. 2
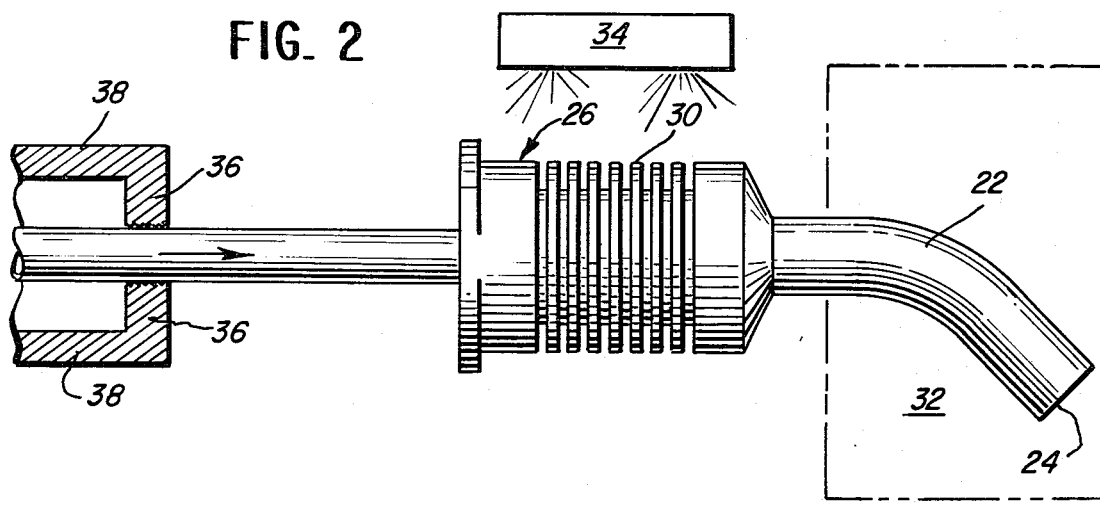
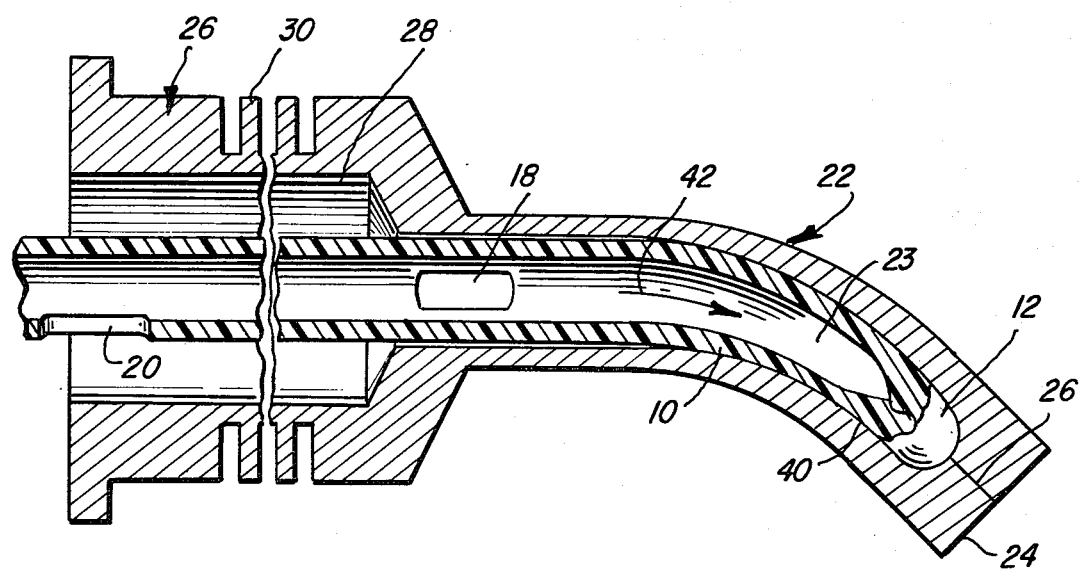
FIG. 3

METHOD AND APPARATUS FOR MAKING COUDE CATHETERS

BACKGROUND OF THE INVENTION

The coude-type catheter, which has been known for many years, utilizes a curved and closed end. This facilitates the easy passage of the catheter, especially in males, through the urethra, by facilitating the bypassing of the sinus junctions, so that the catheter spontaneously enters the neck of the bladder. Commonly, the curved or elbowed end of the coude catheter tapers to a minimum width at its end.

Various types of coude catheters are known, including inflatable Foley-type catheters, as well as simple, noninflatable Robinson-style catheters comprising a single tubular member.

The prior art coude catheters have the disadvantage of being expensive to manufacture. Accordingly, though they are very desirable for use in self-insertion by a layman, for example to assist in urination on a routine basis, the expense of the catheters has inhibited their use.

Latex coude catheters are generally made by dipping on a mold which defines the curved end, as well as the rest of the catheter. Also, coude catheters have been made by casting the catheter tip in contact with the end of catheter tubing, so that the tip becomes a sealed end portion for a catheter tube. Polyvinyl chloride and plasticizer in a liquid form have been used for this purpose. The cure to solidification takes place by heating to form the final, joined, two-piece catheter.

Disadvantages of the above are found, in that it is difficult to obtain a smooth transition between the cast head and the body of the catheter without irregularities and the like, which are quite undesirable in a urinary drainage catheter. Also, a risk exists of separation of the cast head from the catheter body when inserted in the bladder.

By this invention, a molding technique is provided in which a single piece of thermoplastic, flexible tubing is converted into a catheter having a coude-type end without the use of a separate, cast piece, or without the laborous and time-consuming dipping technique, which requires multiple dipping steps to obtain the desired catheter.

DESCRIPTION OF THE INVENTION

In accordance with this invention, an elbowed-end or coude catheter may be made by inserting an end of a flexible, thermoplastic tube into the bore of a closed-end, hollow tubular die which defines the desired curve of the elbowed-end catheter. The die is heated to a temperature above the plastic melt temperature of the thermoplastic tube, while the tube is advanced into the die to cause generally at least 0.5 cm., and preferably no more than about 2 cm., of the tube end to collapse into a generally solid, curved mass.

The die is then cooled in any desired manner, along with the tube, to a temperature which is below, and preferably substantially below, the plastic melt temperature. Thereafter the tube is withdrawn from the die.

Aperture means may be conventionally formed in the wall of the tube adjacent the curved end by punching either before or after the process described above, for fluid communication between the interior and the exterior of the tube.

Preferably, the thermoplastic tube defines a Shore 'A' durometer of at least 65, and preferably no more than 100. At durometer levels of less than 65, the tubing tends to buckle as one attempts to advance it into the die for collapsing and curving of the end of the tube. At durometer values of above 100, the material is frequently too stiff for normal use as a catheter, although the device may find use in other fields.

Preferably, the process of this invention can be performed with a radio frequency (RF) sealing machine, for example, of the type sold by the Radio Frequency Company of Medfield, Mass. In that apparatus, the tubing is inserted into the closed-end, hollow, tubular die with a portion of the tubing being clamped by a transfer mechanism, which automatically advances the tubing into the die at the predetermined rate of advance, which is preferably from about 0.14 to 0.63 inch per second.

The curved die, which may be made of brass or the like, may then be exposed to a high frequency magnetic field to heat the die by induction, or otherwise heated. The heat passes to the thermoplastic tube end by conduction, and, as the tube end begins to melt, the transfer mechanism is advanced, generally at a predetermined time after heating begins, which is preferably from about 0.1 to 12 seconds. Preferably, the entire heating time as operated on the RF sealing machine described above is from 5 to 15 seconds, specifically about $5\frac{3}{4}$ seconds, with an outside mold temperature reaching from 300° to 500° F., specifically about 410° F.

As a result of this, the tip of the tubing collapses from its outer end inwardly, with the air in the bore of the tube being appropriately displaced. It is generally desirable to find specific optimal parameters of conditions which will provide the desired collapse. For example, if the advancement rate is too fast, the tubing may tend to buckle. If it is too slow, the tubing may tend to collapse prematurely, blocking air to provide large bubbles in the tip.

Specific conditions for polyvinyl chloride tubing of about 3/16 inch outer diameter and $\frac{1}{8}$ inch inner diameter include a mold temperature of 410° F., a feed rate of advancing the tube into the die of 11/16 inch over a period of three seconds, commencing 2 seconds after iniations of heating, and a heating time of $5\frac{3}{4}$ seconds, in which the R.F. energy is applied to the closed-end, hollow tubular die.

After the $5\frac{3}{4}$ second pulse of R.F. energy has been applied, focused at the hollow tubular die, the heat quickly dissipates from the hollow tubular die to the rear sleeve, which is preferably of larger mass so that the tubular die may quickly cool. The rear sleeve may either be air-cooled, or, if desired, it may be cooled with water, carbon dioxide or Freon, for example, to speed up the manufacturing cycle of this process.

Accordingly, the tubular die may intermittently be heated in a production process, followed by intermittent cooling of the more massive sleeve that it may carry adjacent its rear end, so that the manufacturing mass production process may continue on a rapid cyclic basis.

In the drawings,

FIG. 1 is an elevational view of a coude catheter which may be made in accordance with this invention.

FIG. 2 is an elevational view, partly schematic, showing how the catheter may be held and advanced into the die, and how R.F. energy may be applied to the hollow tubular die in a cyclic manner while cooling fluid may be applied to the rear sleeve attached to the die between the applications of cycles of R.F. energy.

FIG. 3 is a detailed longitudinal sectional view of the die of this invention, showing the tubing in the process of being advanced and collapsed at its tip.

Referring to the drawings, FIG. 1 shows a catheter 10 which may be made in accordance with this invention, utilizing the preferred parameters described above. Catheter 10 may be a simple extruded tubing of polyvinyl chloride plastic material having a Shore 'A' durometer value of about 77, or any other desired flexible, thermoplastic material, for example, having, as stated above, an outer diameter of approximately 3/16 of an inch and an inner diameter of about ⅛ inch.

Coude tip 12 is shown to be generally solid with the bore 15 of catheter 10 terminating at distal end wall 14. However, optical discontinuities 16, which appear to be fold lines of the plastic, are often seen in the solid tip 12 of catheter 10.

Apertures 18, 20, positioned preferably at 90° from each other about the axis of catheter 10, are provided for communication through the wall of catheter 10.

As stated above, this very inexpensive catheter is particularly suited for self-catheterization on the part of individuals who otherwise would need special medical care, the catheter being reliable and inexpensive for regular, one-time, throw-away use.

FIG. 2 schematically shows a typical mechanism which may be utilized to support and advance thermoplastic tubing 10 into the die of this invention. The specific mechanism used may be the machine described previously.

Closed end, hollow tubular die 22 may be made of brass or equivalent material, and is proportioned to snugly receive tubing 10 in its bore 23 as it is advanced.

Closed end 24 of die 22 may define an optional air bleed hole 26 to facilitate in removal of the air, as may be desired.

At the end of die 22 opposite from closed end 24, an enlarged sleeve member 26, which may advantageously be more massive than die member 22 and integrally attached thereto, with both members 22 and 26 being made of a single piece of brass. Thus, sleeve member 26, having an enlarged bore 28 relative to the bore 23 of die member 22, may serve as a heat sink to receive and absorb heat generated by radio frequency energy, for example, in the die member 22. Alternatively, other forms of energy generation may be utilized, including direct flame application to member 22 and the like. Annular radiating fins 30 are provided on the exterior of sleeve member 26 to facilitate the cooling of the member.

R.F. energy applying means 32, of conventional design, is shown in phantom, being preferably focused adjacent the outer end of hollow tubular die 22 for rapid heating thereof in a single pulse of preferably 5 to 15 seconds, with the heat then quickly dissipating into sleeve 26.

Preferably, only approximately the outer half of die 22 is heated to a temperature sufficient to raise the catheter tip 12 to a temperature above its plastic melt temperature, so that the portion of plastic tubing in the inner portion of die 22 may be generally unaffected.

While sleeve 26 may be simply air-cooled if desired, water may be applied, for example through a conventional application means 34 to accelerate the cooling. Also, frozen carbon dioxide may be applied in a spray to sleeve 26, to accelerate the cooling. As a further alternative, a Freon material may be applied to sleeve 26 to the same effect.

Preferably, if air cooling is used with the specific parameters of the operation described above, at least about 18 seconds of cooling time is desirable following the 5¾ second application of R.F. energy. If water cooling is used, the cooling time may be reduced to about 15 seconds, while application of frozen carbon dioxide can reduce the cooling time to a figure on the order of 5 to 7 seconds.

Clamp member 36 grasps tubing 10, and may be advanced by rods 38 at a predetermined rate for a predetermined distance, as specified above. The clamp member may be a stock part of the R.F. sealing machine described above for the desired precise advancement of tubing 10 into die 22, as the end of the tubing progressively collapses, as in FIG. 3, to provide more material to the collapsed end, to build it to the desired proportions.

Bore 23 of closed-end hollow curved or elbowed tubular die 22 can be seen from FIG. 3 to have bore portion 40 which tapers outwardly to a minimum width to provide the desired tapered shape to the coude tip of the catheter. As the tube is advanced, as shown in FIG. 3 by arrow 42, the collapse begins at the outer end of tube 10, and proceeds for the desired distance inwardly as the tubing is advanced, driving essentially all of the air into the remaining bore of tubing 10, so that significant air bubbles are not entrapped in the essentially-solid curved tip 12.

After the requisite cooling time has elapsed, grasping member 36 may be retracted, to remove tube 10 and its newly-formed tip 12 from the die 22.

It is also preferred to apply a mold release agent to at least the end of plastic tubing 10 prior to processing in accordance with this invention. This can be accomplished by dipping the tip of the plastic tubing, for example, into a liquid Freon solution which contains one half percent by weight of a dimethylpolysiloxane liquid, which is a known mold release material. Specifically, Freon TF is suitable for this purpose.

By this invention, coude catheters of any type, with or without an inflation balloon, and made of a thermoplastic material, may be manufactured quickly and efficiently for a new, low-cost product, to bring the benefits of the coude catheter into wider use.

For example, catheters similar to those disclosed in U.S. Pat. No. 4,154,244 may be made in accordance with this invention into coude-type catheters for combined advantages in accordance with this invention.

The above has been offered for illustrative purposes only, and is not intended to limit the invention of this application, which is as defined in the claims below.

That which is claimed is:

1. The method of making a elbowed-end catheter which comprises: inserting a end of a flexible, thermoplastic tube into the bore of a closed-end, hollow, tubular one piece die which defines the desired curve of the elbowed-end catheter; heating said tubular die to a temperature above the plastic melt temperature of said thermoplastic tube, while advancing said tube into the die, to cause at least 0.5 cm. of the tube end to collapse into a curved mass; cooling said die and tube to a temperature below said plastic melt temperature; and withdrawing said tube from the die.

2. The method of claim 1 in which aperture means is formed in the wall of said tube adjacent said end for fluid communication between the interior and exterior of said tube.

3. The method of claim 1 in which said thermoplastic tube defines a Shore 'A' durometer of at least 65.

4. The method of claim 1 in which the bore of the closed-end, hollow, tubular die defines an outer closed end portion that tapers outwardly to a minimum width.

5. The method of claim 1 in which said tube end collapses into a generally solid, curved mass.

6. The method of making a elbowed-end catheter which comprises: inserting an end of a flexible, thermoplastic tube into the bore of a closed-end, hollow tubular one piece die which defines the desired curve of the elbowed-end catheter, and which bore further tapers outwardly toward its closed end to a minimum width, the Shore 'A' Durometer of said flexible thermoplastic tube being at least 65; heating said tubular die to a temperature above the plastic melt temperature of said thermoplastic tube while advancing said tube into the die, to cause at least 0.5 cm. of the tube end to collapse into a curved mass; cooling said die and tube to a temperature below said plastic melt temperature; and withdrawing said tube from the die.

7. The method of claim 6 in which aperture means is formed in the wall of said thermoplastic tube adjacent said end for fluid communication between the interior and exterior of said tube.

8. The method of claim 7 in which said thermoplastic tube is made of a polyvinyl chloride plastic material.

9. The method of claim 7 in which said hollow tubular die is heated to a temperature of 300° to 500° F.

10. The method of claim 7 in which said thermoplastic tube is advanced into the die, to cause the tube end to collapse, at a rate of 0.14 to 0.63 inch per second.

11. The method of claim 7 in which said die is heated with radio frequency radiation for a period of 5 to 15 seconds.

12. The method of claim 7 in which said thermoplastic tube is treated, prior to insertion into the bore of said die, with a lubricant.

13. The method of claim 7 in which said hollow tubular die defines an enlarged sleeve portion integral therewith, and positioned remote from said closed end of the hollow tubular die, said sleeve portion defining integral heat loss fins, said sleeve being positively cooled during said cooling step by means of a cooling agent.

14. The method of claim 6 in which said tube end collapses into a generally solid, curved mass.

15. The method of claim 6 in which Shore "A" Durometer of said thermoplastic tube is no more than 100.

* * * * *